United States Patent [19]

Wille

[11] 4,104,202

[45] Aug. 1, 1978

[54] PERFUME COMPOSITIONS AND PROCESS FOR PREPARING SAME

[75] Inventor: Hans J. Wille, Naarden, Netherlands

[73] Assignee: Naarden International N.V., Naarden-Bussum, Netherlands

[21] Appl. No.: 776,764

[22] Filed: Mar. 11, 1977

[30] Foreign Application Priority Data

Mar. 15, 1976 [NL] Netherlands .......................... 7602686

[51] Int. Cl.$^2$ .............................................. C11B 9/00
[52] U.S. Cl. .................................... 252/522; 568/875; 568/840; 568/879; 560/249; 560/261
[58] Field of Search .......... 260/488 H, 632 R, 638 G; 252/522

[56] References Cited

U.S. PATENT DOCUMENTS 3,856,867  12/1974  Ramsden .......................... 260/632 R

FOREIGN PATENT DOCUMENTS 544,388    2/1932   Fed. Rep. of Germany.
6,811,388  2/1969   Netherlands.
516,494   12/1971   Switzerland.
1,381,027  1/1975   United Kingdom.

OTHER PUBLICATIONS

Hariel, Chem. Abs. 72, 24504.
Ali, Chem. Abs. 70, 60746.
Arctander, Perfume & Flavor Chemicals (1969), Items 1794 and 1803.

*Primary Examiner*—C. Davis
*Attorney, Agent, or Firm*—Brumbaugh, Graves, Donohue & Raymond

[57] ABSTRACT

The invention relates to the preparation of perfume compositions. More specifically the invention relates to the use of new 1,5-alkadien-4-ols and esters derived therefrom as components of such compositions.

15 Claims, No Drawings

PERFUME COMPOSITIONS AND PROCESS FOR PREPARING SAME

Fragrance compounds with a naturally green odor are highly esteemed in the perfume industry. Such fragrance compounds are mostly natural in origin and thus a sufficient supply is not always available. Moreover, the quality of these naturally occurring fragrance compounds tend to vary. Accordingly a growing demand exists for synthetic fragrance compounds which can replace these natural compounds.

It has now been found that new 1,5-alkadienols and esters derived therefrom, having the general structural formula:

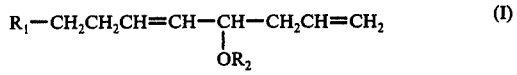

wherein $R_1$ is an alkyl group having from 1 to 4 carbon atoms and $R_2$ is selected from the group consisting of hydrogen (dienols), formyl radicals and alkyl carbonyl radicals, the alkyl portion of which has from 1 or 2 carbon atoms (dienol esters), are valuable fragrance compounds.

Of these novel compounds, those where $R_1$ is a straight chain (unbranched) alkyl group having from 1 to 3 carbon atoms are preferred. Especially important among the compounds of formula I are the alcohols ($R_2$ = H) and acetates ($R_2$ = $COCH_3$). One of the novel compounds of the present invention is 1,5-nonadien-4-ol. This compound has a green, slightly earthy and mushroom-like odor. Another specific compound of the present invention is 1,5-undecadien 4-ol and the corresponding acetate; both have a green and slightly fatty odor. The odor of this acetate is particularly suggestive of galbanum.

According to the present invention the 1,5-alkadien-4-ols may be prepared by reacting an α,β-unsaturated aldehyde having the structural formula

and wherein $R_1$ has the same meaning as $R_1$ in formula I above, with allyl-magnesium chloride

The reaction scheme is as follows:

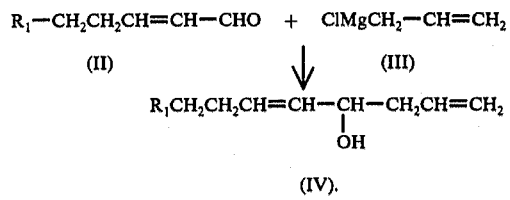

The alcohols thus obtained may be converted into esters in accordance with esterification procedures well known in the art.

The compounds according to the invention are strong and stable fragrance compounds with a long lasting odor. As such, they may be incorporated successfully in perfume compositions. The term "perfume composition" as used herein means a mixture of organic compounds, such as aldehydes, ketones, alcohols, carboxylic acids, esters, nitriles, essential oils, etc., which is used, as such or after dilution with a suitable solvent or in combination with a solid substrate, to impart a desired odor to the skin or to products such as air freshener sprays, deodorants, soap, detergents, cosmetics, etc.. According to the present invention, the amount of the novel 1,5-alkadien derivative to be used in said perfume compositions or products may vary widely, depending upon the specific composition, the type and quantity of the other components of the composition and the desired odor effect. Some of the compounds of the invention have such strong odors that they will have a clearly perceptible positive effect upon a perfume composition when added in quantities as low as about 100 parts per million. However, in some cases quantities of up to about 15% by weight may be used in perfume compositions to achieve specific odors. These quantities apply to pure perfume compositions. On dilution with a solvent or a substrate, or on application in a product to be perfumed, these quantities are proportionally lower, depending on the quantity of perfume composition that is used.

EXAMPLE I

Synthesis of 1,5-undecadien-4-ol

A mixture of 300 ml of tetrahydrofuran, 21 g of magnesium, 0.07 g of iodine and 2 g of allyl chloride in a nitrogen atmosphere is carefully heated to 35° C under constant stirring. When the reaction has started, a mixture of 700 ml of tetrahydrofuran, 58.2 g of allyl chloride and 100.8 g of 2-octenal is carefully added in 3 hours. During this addition the temperature is kept at 30°–35° C, if necessary by cooling with a waterbath. The stirring of the reaction mixture at this temperature is continued for another 1.5 hours. After cooling the reaction mixture to room temperature, it is poured in a mixture of 80 g of acetic acid, 800 g of ice and 200 ml of toluene.

The total mixture is stirred vigorously, the water layer is separated and extracted with 100 ml of toluene. The combined organic layers are washed with water, 5% soda-solution and again with water. The solvent is evaporated and the residue is distilled under reduced pressure. 80.6 g of 1,5-undecadien-4-ol is obtained (64%); b.p. 75°–78° C/2 Torr; $n_{20}^D$ = 1.4568.

EXAMPLE II

Synthesis of 1,5-nonadien-4-ol 0.1 Mole of allyl-magnesium chloride, prepared from 0.1 mole of allyl chloride and magnesium in excess, is added carefully to a solution of 0.1 mole of 2-hexenal in 50 ml of tetrahydrofuran at 5° C. The reaction mixture is subsequently stirred at room temperature for 1 hour. The reaction mixture is hydrolyzed by pouring it into a mixture of ice and acetic acid in excess.

The whole mixture is subsequently extracted with toluene and the solution in toluene is washed until neutral with 5% soda-solution. The solvent is evaporated and the residue distilled under reduced pressure. 1,5-Nonadien-4-ol is obtained in 65% yield; b.p. 77° C/10 Torr; $n_{20}^D$ = 1.4548.

EXAMPLE III

Synthesis of 1,5-undecadien-4-yl acetate 36 g of 1,5-undecadien-4-ol is stirred and heated to reflux with 32.6 g of acetic acid anhydride for 1 hour. The excess anhydride and the resulting acetic acid are removed by distillation under reduced pressure. The residue is fractionated. Yield: 33.8 g (76%) 1,5-undecadien-4-yl acetate; b.p. 70°–80° C/2 Torr; $n_{20}^D =$ 1.4468. 1,5-Nonadien-4-yl acetate was prepared in a similar way; yield: 75%; b.p. 85° C/10 Torr; $n_{22}^D =$ 1.4403.

EXAMPLE IV

A perfume composition of the lavender-type was prepared according to the following recipe:

```
300 parts by weight Lavender oil French
270 parts by weight Bergamot oil, Bergaptene-free
100 parts by weight Geranium oil
100 parts by weight Isononyl acetate
 70 parts by weight Dihydromyrcenol
 50 parts by weight Rhodinol
 30 parts by weight Musk Ambrette
 20 parts by weight Musk R₁¹⁾
 20 parts by weight Patchouly oil
 20 parts by weight Mysorol²⁾
 Parts by weight 1,5-nonadien-4-ol (10% in ethanol)
1000 parts by weight.
```

[1] Perfume compound of Naarden International, see British Pat. No. 981,838
[2] Sandalwood perfume compound of Naarden International.

EXAMPLE V

A perfume composition of the "Men's cologne" type was prepared according to the following recipe:

```
285 parts by weight Bergamot oil, Bergaptene-free
180 parts by weight Lemon oil
 50 parts by weight Vetiveryl acetate
 50 parts by weight α-Amylcinnamaldehyde
 30 parts by weight Jasmin N.B. 133¹⁾
 25 parts by weight Methyl dihydrojasmonate
 50 parts by weight Lavender concrete
 10 parts by weight Musk R₁²⁾
 10 parts by weight Oakmoss absolute
 30 parts by weight Acetylcedrene
 30 parts by weight Sandalwood oil
 40 parts by weight Hydroxycitronellal
 30 parts by weight α-Isomethyl-ionone
 30 parts by weight Mysorol³⁾
 50 parts by weight Tincture of Civet
 70 parts by weight Orange oil Florida
 30 parts by weight 1,5-undecadien-4-yl acetate
1000 parts by weight.
```

[1] Jasmin perfume base of Naarden International.
[2] Perfume compound of Naarden International, see British Pat. No. 981,838.
[3] Sandalwood perfume compound of Naarden International.

I claim:

1. A compound for use in a perfume composition having the structural formula

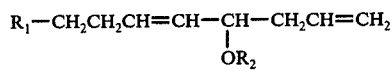

wherein $R_1$ is an alkyl radical having from 1 to 4 carbon atoms and $R_2$ is selected from the group consisting of hydrogen and formyl radicals and alkyl carbonyl radicals, the alkyl portion of which has 1 or 2 carbon atoms.

2. A compound according to claim 1, wherein $R_1$ is an unbranched alkyl radical having from 1 to 3 carbon atoms.

3. A compound according to claim 2 wherein $R_2$ is a $CH_3CO$-radical.

4. The compound, 1,5-nonadien-4-ol, for use in perfume compositions.

5. The compound, 1,5-undecadien-4-yl acetate for use in perfume compositions.

6. A perfume composition which comprises having added thereto as a fragrance, at least one alkadiene compound having the structural formula:

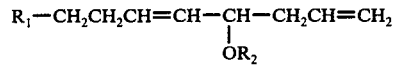

wherein $R_1$ is an alkyl radical having from 1 to 4 carbon atoms and $R_2$ is selected from the group consisting of hydrogen and formyl radicals and alkyl carbonyl radicals, the alkyl portion of which has from 1 to 2 carbon atoms.

7. A composition according to claim 6, wherein $R_1$ of said alkadiene compound is an unbranched alkyl radical having from 1 to 3 carbon atoms.

8. A composition according to claim 7, wherein $R_2$ of said alkadiene compound is a $CH_3CO$ radical.

9. A composition according to claim 6, wherein the amount of the alkadiene compound present in the perfume composition is from about 100 ppm to about 15% by weight.

10. A perfume composition which comprises having added thereto as a fragrance, 1,5-nonadiene-4-ol.

11. A perfume composition which comprises having added thereto as a fragrance, 1,5-undecadien-4-yl acetate.

12. A process for the preparation of perfume compositions comprising incorporating as a fragrance, at least one alkadiene compound with substances suitable for inclusion in perfume compositions, said compound having the structural formula:

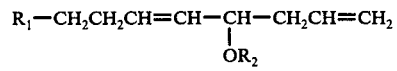

wherein $R_1$ is an alkyl radical having from 1 to 4 carbon atoms and $R_2$ is selected from the group consisting of hydrogen, formyl radicals and alkyl carbonyl radicals, the alkyl portion of which has from 1 to 2 carbon atoms.

13. A process according to claim 12, wherein $R_1$ of said alkadiene compound is an unbranched alkyl radical having from 1 to 3 carbon atoms.

14. A process according to claim 13, wherein $R_2$ of said alkadiene compound is a $CH_3CO$-radical.

15. A process according to claim 12, wherein the amount of the alkadiene compound used in the perfume compositions is from about 100 ppm to about 15% by weight.

* * * * *

UNITED STATES PATENT OFFICE
CERTIFICATE OF CORRECTION

Patent No. 4,104,202　　　　　　　　Dated August 1, 1978

Inventor(s) Hans J. Wille

It is certified that error appears in the above-identified patent and that said Letters Patent are hereby corrected as shown below:

Column 3, line 21, "Parts" should read -- 20 parts --.

Signed and Sealed this

Thirtieth Day of January 1979

[SEAL]

Attest:

RUTH C. MASON
Attesting Officer

DONALD W. BANNER
Commissioner of Patents and Trademarks